US00PP12772P2

(12) United States Plant Patent
Trujillo

(10) Patent No.: US PP12,772 P2
(45) Date of Patent: Jul. 16, 2002

(54) TARO PLANT NAMED 'PA'AKALA'

(75) Inventor: Eduardo E. Trujillo, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 0 days.

(21) Appl. No.: 09/426,560

(22) Filed: Oct. 22, 1999

(51) Int. Cl.[7] ..... A01H 5/00
(52) U.S. Cl. ..... Plt./258
(58) Field of Search ..... Plt./258

(56) References Cited

U.S. PATENT DOCUMENTS

| | | | | |
|---|---|---|---|---|
| PP6,000 | P | 9/1987 | Christensen | Plt./130 |
| PP6,895 | P | 7/1989 | Meilland | Plt./137 |
| 4,925,696 | A | 5/1990 | Slimak | 426/637 |
| 5,034,327 | A | 7/1991 | Takayama et al. | 435/240.4 |
| PP8,526 | P | 12/1993 | Wilfret | Plt./373 |
| 5,464,646 | A | 11/1995 | Huang et al. | 426/615 |
| PP10,466 | P | 6/1998 | Wilfret | Plt./373 |

OTHER PUBLICATIONS de la Pena, R. S. "The University of Hawaii Taro Germplasm Nursery and Breeding Program" Proceddings of the Workshop on Taro and Tanier Modeling University of Hawaii Research Extension Series 136, pp. 7–9, Aug. 1992.*

Whitney, L. D. et al. "Taro Varietes in Hawaii" Hawaii Agricultural Experiment Station Bulletin No. 84. pp. 1–86, Dec. 1939.*

* cited by examiner

*Primary Examiner*—Bruce R. Campell
*Assistant Examiner*—Wendy Baker
(74) *Attorney, Agent, or Firm*—Medlen & Carroll LLP

(57) ABSTRACT

The present invention relates to a new and distinct variety of *Colocasia esculenta* (popularly known as taro) named 'Pa'kala'. 'Pa'akala' differs distinctively from other plants by its unique combination of resistance to taro leaf blight caused by *Phytophthora colocasiae*, high tolerance to root rot caused by Pythium ssp., vigorous growth, extra-large mother corm size, and pinkish corm of very good flour quality and good poi and eating qualities.

6 Drawing Sheets

The present invention relates to a new and distinct variety of *Colocasia esculenta* (popularly known as taro) named 'Pa'akala'. 'Pa'akala' plants were produced by cross-pollination of the commercial cultivars 'Ngeruuch' and 'Maui Lehua' selection of progeny for a single plant which exhibited desirable agronomic and disease resistance properties, and asexual reproduction of the selected plant using tissue culture and propagation of hulis. 'Pa'akala' differs distinctively from other taro plants by its unique combination of resistance to taro leaf blight (TLB) caused by *Phytophthora colocasiae*, high tolerance to root rot caused by Pythium spp., vigorous growth, extra-large mother corm size, and pinkish corm of very good flour quality and good poi and eating qualities.

REPRODUCTION

'Pa'akala' is a product of the taro-breeding program of the University of Hawaii, Honolulu, Hi. The 'Pa'akala' cultivar was derived from a single plant which was selected from a cross between the Hawaiian taro cultivar 'Maui Lehua' (unpatented) and the Palauan taro cultivar 'Ngeruuch' (unpatented; also referred to as 'P10'). Ancestry of both parents is unknown, except that 'Maui Lehua' belongs to the Group Lehua of Hawaiian-Polynesian taros and is susceptible to taro leaf blight (TLB), caused by *Phytophthora colocasiae*, and 'Ngeruuch' is a Micronesian taro from Palau and is highly resistant to this disease.

'Maui Lehua,' the preferred poi taro of Hawaii, was selected as the female parent; 'Maui Lehua' exhibits the desirable agronomic characteristics of absence of runners, less than 6 suckers per plant, and superior poi quality purple corm. 'Ngeruuch' was selected as the pollen parent for its high resistance to the taro leaf blight disease; 'Ngeruuch' exhibits undesirable vegetative proliferation by long stolons. Both parents are commercial cultivars. The initial cross-pollination of 'Ngeruuch' pollen and 'Maui Lehua' female flowers was made to produce a new poi taro having the agronomic characteristics of 'Maui Lehua' and the resistance to TLB of 'Ngeruuch.' $F_1$ progeny plants (including a single plant which was later designate 'Pa'akala') were selected for their disease resistance to TLB, pocket rot, and basal rot, having fewer than 6 suckers and no runners, poi quality, and taste of cooked corms.

Asexual reproduction of 'Pa'akala' was performed in Honolulu, Hi., by apical meristem multiplication using standard tissue culture procedures [Keolanui et al. (1993) Handbook for commercial-scale taro (*Colocasia esculenta*) tissue culture in Hawaii. University of Hawaii, College of Tropical Agriculture and Human Resources, Research Extension Series 145]. The traits of the plants which were generated by apical meristem multiplication were identical to those of the plant from which they were asexually reproduced. Cloned and rooted tissue culture plants of 'Pa'akala' were produced at the University of Hawaii at Manoa, Honolulu, Hi.

Rooted tissue culture plants were grown to hulis to produce plants for field-testing as follows. Rooted tissue culture plants were transplanted from rooting medium to Sunshine Mix 4 potting soil. Potting mix (10 cubic inches volume) was used per plant in Compak® 606 multi-pots 3.25" deep with cell opening 2.25"×2"(T.O. Plastics Inc, 78th Street, MPLS, Minn. 55425). The Sunshine Mix 4 was mixed thoroughly with 2 lb of fast acting granular lime (The Chas H. Lilly Co, Portland, Oreg. 97283) and 0.5 lb of Osmocote slow release fertilizer 14-14-14 (Scotts-Sierra Horticultural Products Co., 14111 Scottslawn Rd., Marysville, Ohio 43042) per cubic yard prior to use. The cells were placed in T.O. Plastics trays without holes 20.25"×15.75"×2.5" in size, containing a liquid nutrient solution made with one teaspoon of Peters (Scotts-Sierra) all-purpose soluble plant food 20-20-20/gallon of water. Plants were grown for 3–4 months in a greenhouse at 28° C. until the stem base of the plants was one inch in diameter and the plants were ready for field planting.

Plants were also propagated in Hakalau, Hi., by the farming practice known as huli production whereby the apical shoots are separated from the rhizomes by cutting the shoot at the top of the corm immediately above the newest leaf scar and planted. A large number of plants of the new variety have been reproduced by this method and the resulting plants have exhibited the distinguishing characteristics of the original plant which was used for asexual propagation, indicating that the new 'Pa'akala' cultivar is established.

CHARACTERISTICS

Figure 1:
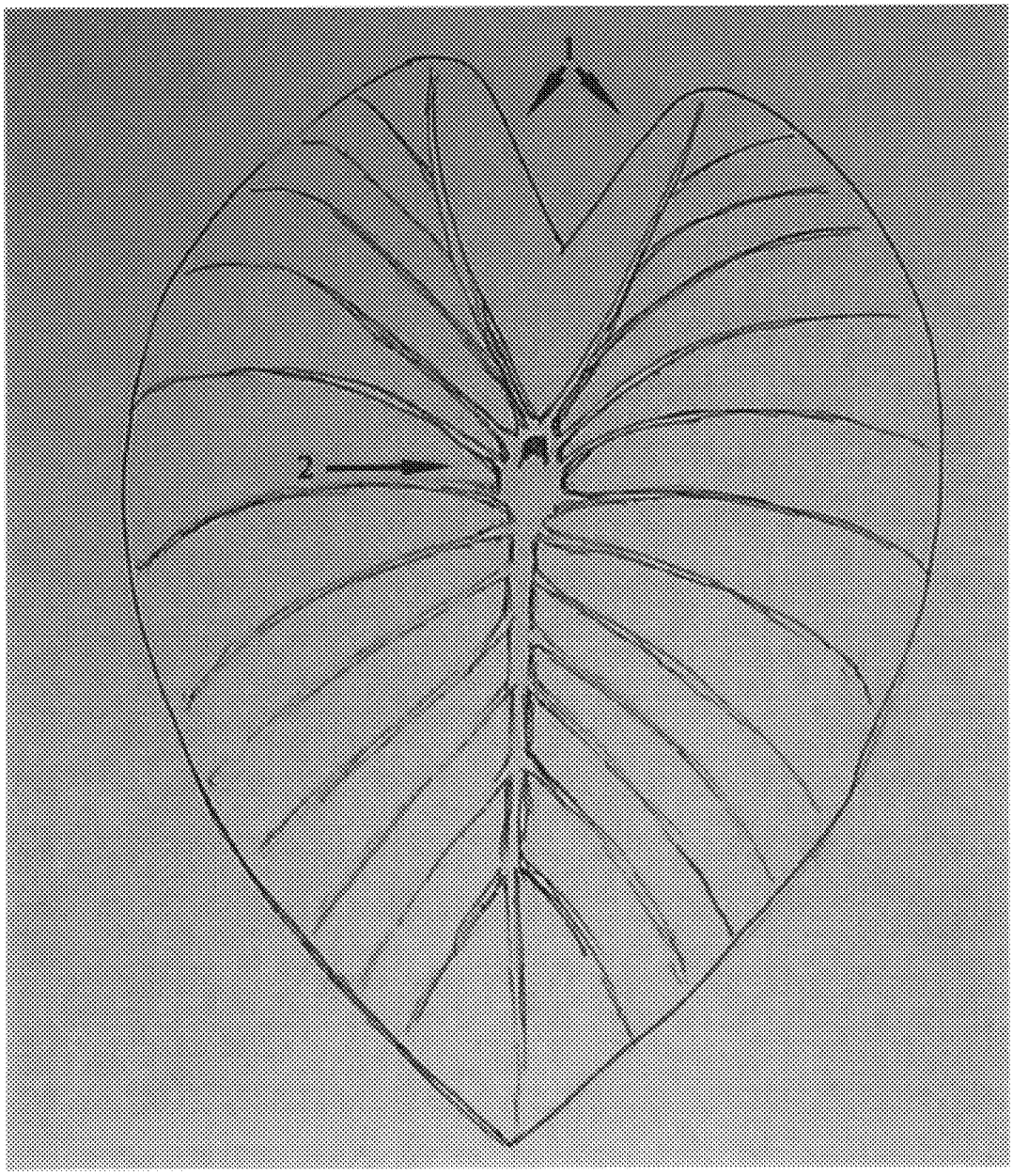
FIG. 1 is a diagram of a leaf which has been laid flat on a horizontal surface, showing the piko (2) (point of attachment of petiole to the lamina) and the deep sinus (1) between the lobes of the leaf on 'Pa'akala'.
Figure 2:
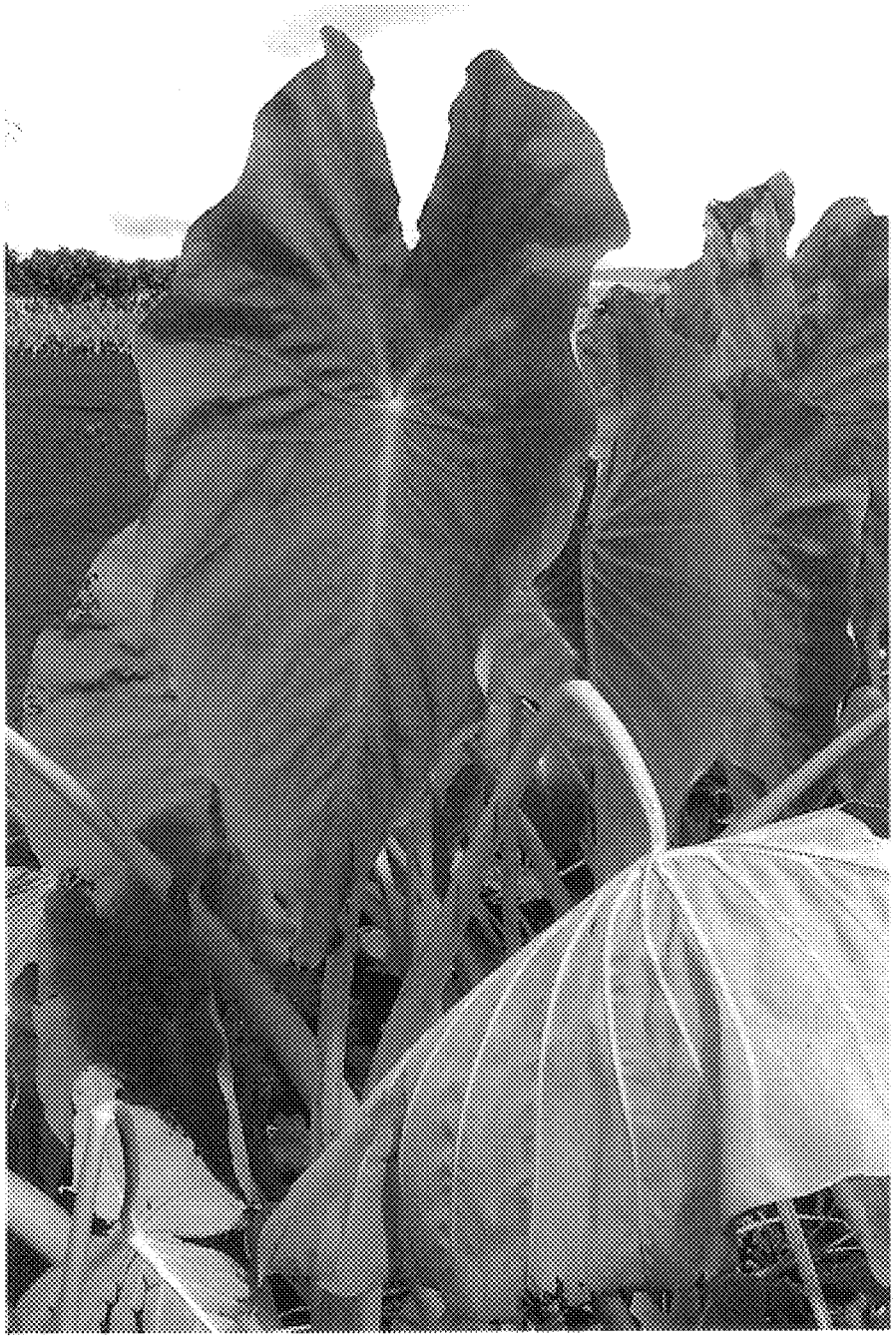
FIG. 2 is a photograph of 'Pa'akala' sagittate-ovate leaf blade with a deep acute 60° angle sinus. Lamina is dark green with light green venation on the abaxial surface, and purplish veins on the adaxial surface, 34 cm wide by 78 cm long.

The asexually reproduced 'Pa'akala' cultivar has several desirable horticultural characteristics, including resistance to taro leaf blight caused by *Phytophthora colocasiae*, high tolerance to root rot caused by Pythium spp., vigorous growth, extra-large mother corm size, and pinkish corm of very good flour quality and good poi and eating qualities. 'Pa'akala' plants are suitable for both upland culture and wetland culture.

Resistance of 'Pa'akala' to TLB was measured in field experiments at the Hakalau Farm and Nursery in Hamakua, Hi., which is located at a 600 ft elevation, receives high precipitation, and has a high incidence of TLB. Four subplots of 'Pa'akala' were planted at 2 elevations in Hamakua, Hi. Each subplot contained 4 rows spaced 4 ft apart with 10 plants/row at a distance of 2 ft between plants. A randomized plot design was used for these tests. Disease assessment consisted of a visual determination of the percent area of foliar TLB damage caused by *Phytophthora colocasiae*. This data is shown in Table 1.

TABLE 1

Percent area of Foliar Damage Caused by *Phytophthora colocasiae*[1]

| Cultivar | First Experiment | Second Experiment | Third Experiment |
|---|---|---|---|
| 'Maui Lehua' | 0.2069 a | 0.2856 a | 0.2800 a |
| 'Pa'akala' | 0.0912 b | 0.0595 cd | 0.0696 b |
| 'Ngeruuch' | 0.0153 c | 0.0320 d | 0.0194 b |

Table 1 shows that 'Pa'akala' shows a significantly high degree of resistance to TLB which is similar to that exhibited by 'Ngeruuch' and which is much greater than that observed by 'Maui Lehua'. Older leaves of 'Pa'akala' show symptoms of hypersensitive reaction when affected by taro leaf blight disease.

Corm yield was also measured in plants planted and harvested in Hamakua, Hi., on Jan. 7, 1999. The mean yield of the main corm of 'Pa'akala' and 'Maui Lehua' was 4.3896 pounds/plant (i.e., 31,868 pounds/acre) and 2.4458 pounds/plant (i.e., 19,126 pounds/acre), respectively. This difference was statistically significant using Tukey's LSD test ($P \leqq 0.05$).

'P'akala' was hightly tolerant to root rot caused by Pythium spp. as distinguished from 'Maui Lehua' which is susceptible to root rot and from 'Ngeruuch' which is resistant to root rot. The number of suckers (3-2) produced by 'Pa'kala' was significantly lower than the number (5-4) produced by 'Ngeruuch'.

Poi quality was measured by determining the stickiness, smoothness, viscosity, taro aroma intensity, and sweetness of the steamed or boiled corm which had been ground and mixed with water to 20% total solids. Desirable poi quality characteristics include a smooth texture, sweet taste, a consistency similar to soft mashed potato, stickiness similar to tapioca pudding, and strong taro aroma. Poi produced from 'Pa'akala' was pinkish beige (compared to purple when prepared from 'Maui Lehua') with good poi quality.

Eating quality was measured by determining the starchiness, and consistency of baked or boiled corms, with a starchy and moist consistency being desirable characteristics. Eating quality of 'Pa'akala' corm was good.

Flour quality was measured by estimating the yield, consistency, and content of oxalic acid of flour prepared from raw taro. Desirable characteristics include high yield, and a consistency similar to commercial wheat flour, that when mixed with sufficient water forms a sticky dough which has a low content of oxalic acid (<0.07% ) and an agreeable sweet flavor. Flour prepared from 'Pa'akala' was creamy white with very good flour quality.

DETAILED BOTANICAL DESCRIPTION

The following combination of traits distinguishes 'Pa'akala' as a new cultivar from other taro cultivars, including the parent plants from which it was derived. The photographs closely approximate the colors of the plants. However, to further facilitate the identification of color, reference is made to the British Color Council and The Royal Horticutural Society, Horticultural Color Chart, except where general color terms of ordinary dictionary significance are obvious. Wherein dimensions, sizes and other characteristics are given, it is to be understood that such characteristics are approximations of averages set forth as accurately as practicable. The descriptions herein are from 3 to 6 month old, as noted, specimens grown in Hakalau, Hi.

Plant:

*Size.*—'Pa'akala' is a vigorous plant, with medium spread. The plant produces up to 5 suckers from rhizomes closely attached to the mother plant or from short stolons in equal proportion. A "mother plant" is the plant material which is first introduced into the soil to begin taro production and which gives rise to a corm, herein referred to as "mother corm". Typically, this plant material contains part of the huli and 2–3 leaf blades. The corm of the mother plant produces rhizomes which give rise to daughter plants which appear above soil level after planting of the mother plant. Plant size is up to a maximum of 1.40 m and 1.80 m high at 3 and 6 months after planting, respectively. Main plant pseudo-stem circumference, at soil line, is up to 33 cm and 54 cm at 3 and 6 months after planting, respectively. Plants were grown on silicate clay soils, with average daily temperature of 27° C., average rainfall of 150 inches/year and average solar radiation of 450 langley (Cal/sq cm/day).

*Maturity.*—12 months from planting to harvest marketable corms.

*Quality.*—Flour quality 4.5 (scale of 1 to 5; 1=poor and 5=excellent). Poi quality 3.5 (scale same as above). Eating quality 4.0 (scale same as above).

Leaves:

*Number.*—Usually, 4–9 month old mother plants maintain 5–6 leaves at a time, each new leaf being produced approximately every 10 days until the corm matures.

*Size.*—Up to 72 cm and 82 cm long, and up to 53 cm and 60 wide on 3 and 6-month-old plants, respectively.

Figure 3:
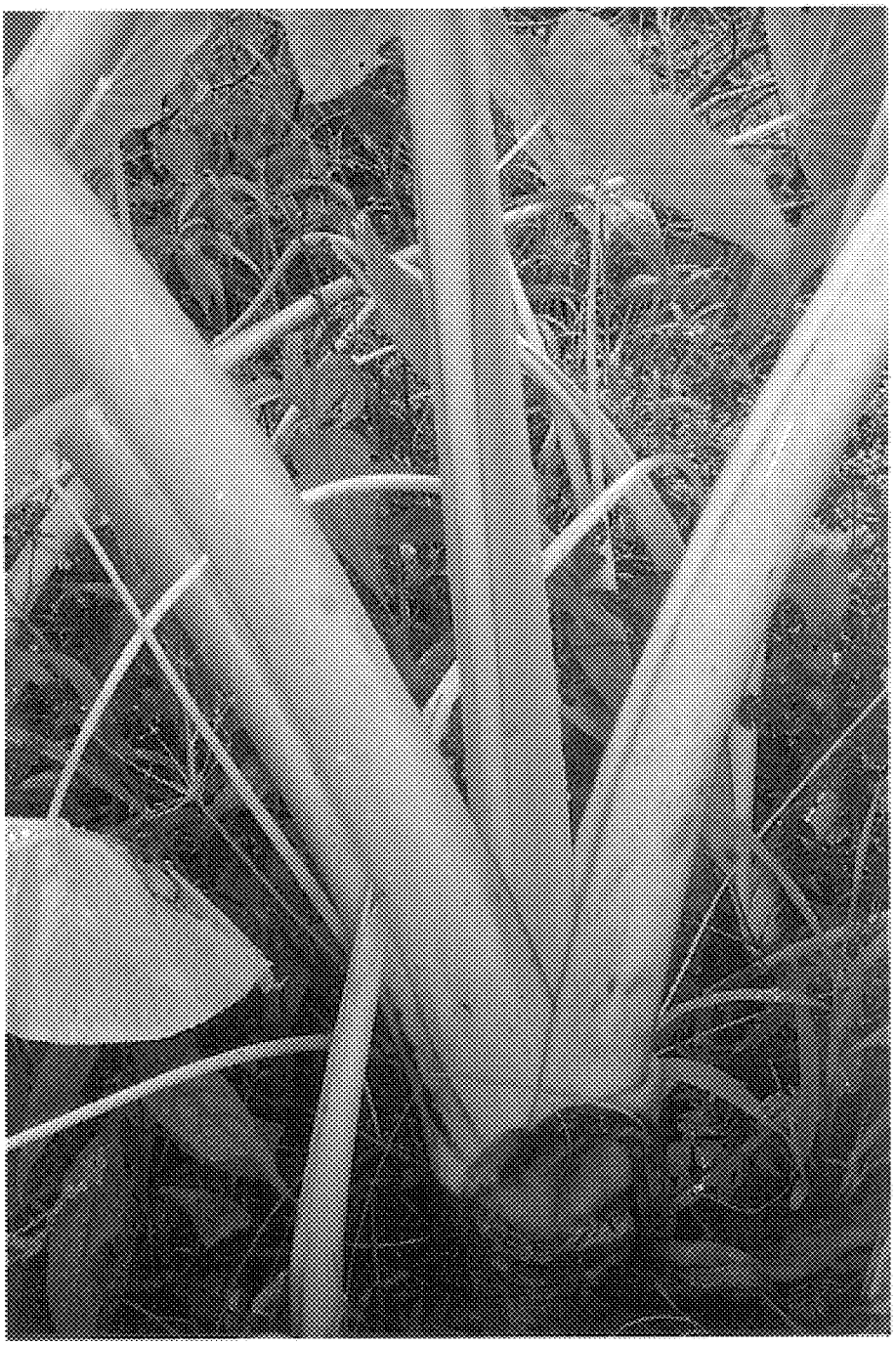
FIG. 3 is a photograph of 'Pa'akala' plant base showing light green petioles with thin purple margins. The petioles measure up to 140 cm long.
Figure 4:
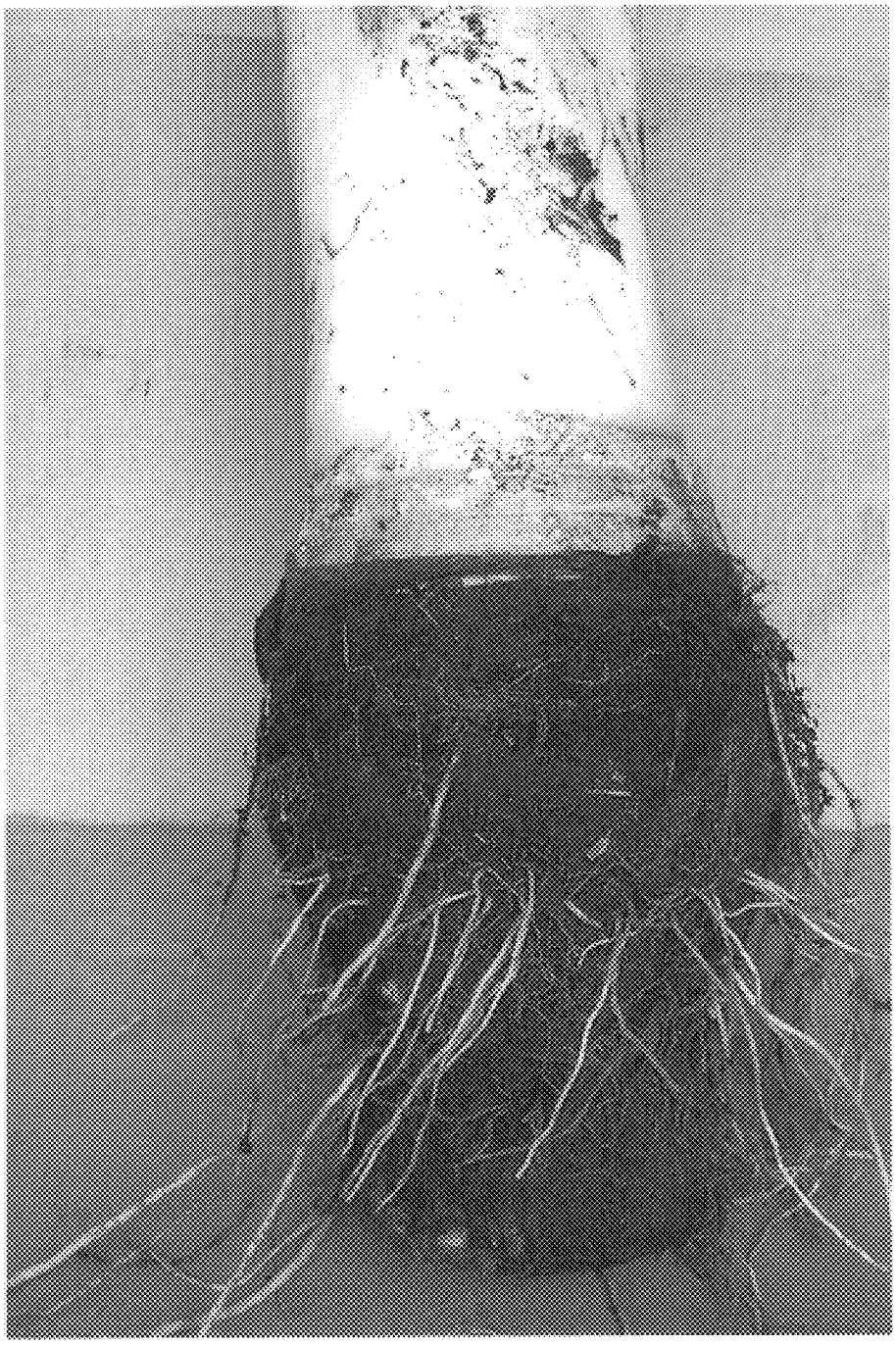
FIG. 4 is a photograph of a 'Pa'akala' ovate shaped corm with pinkish-brown skin and pink roots and pink coloration at the base of huli.
Figure 5:
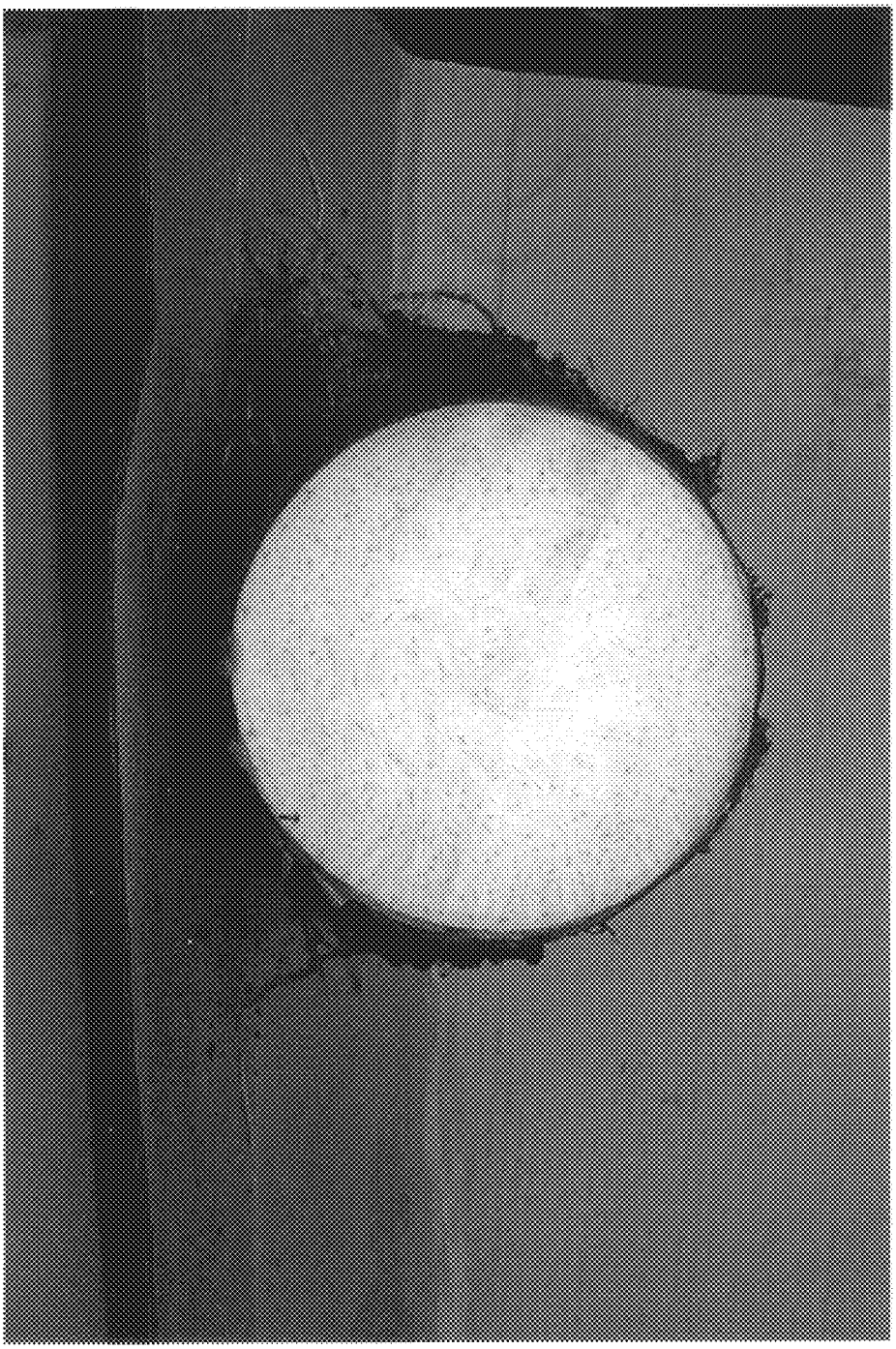
FIG. 5 is a photograph of a cross section of a 'Pa'akala' corm showing pinkish flesh.

*Shape.*—Peltated, erect with apex down and with sagittate-ovate lamina with a deep sinus between lobes of 60° angle, with an entire leaf margin, an acutely pointed apex, and peltate leaf base and palmate-venation (FIG. 1 and FIG. 3). Lamina appendages are absent. Leaf surface is flat. Leaf sheath is open.

Figure 6:
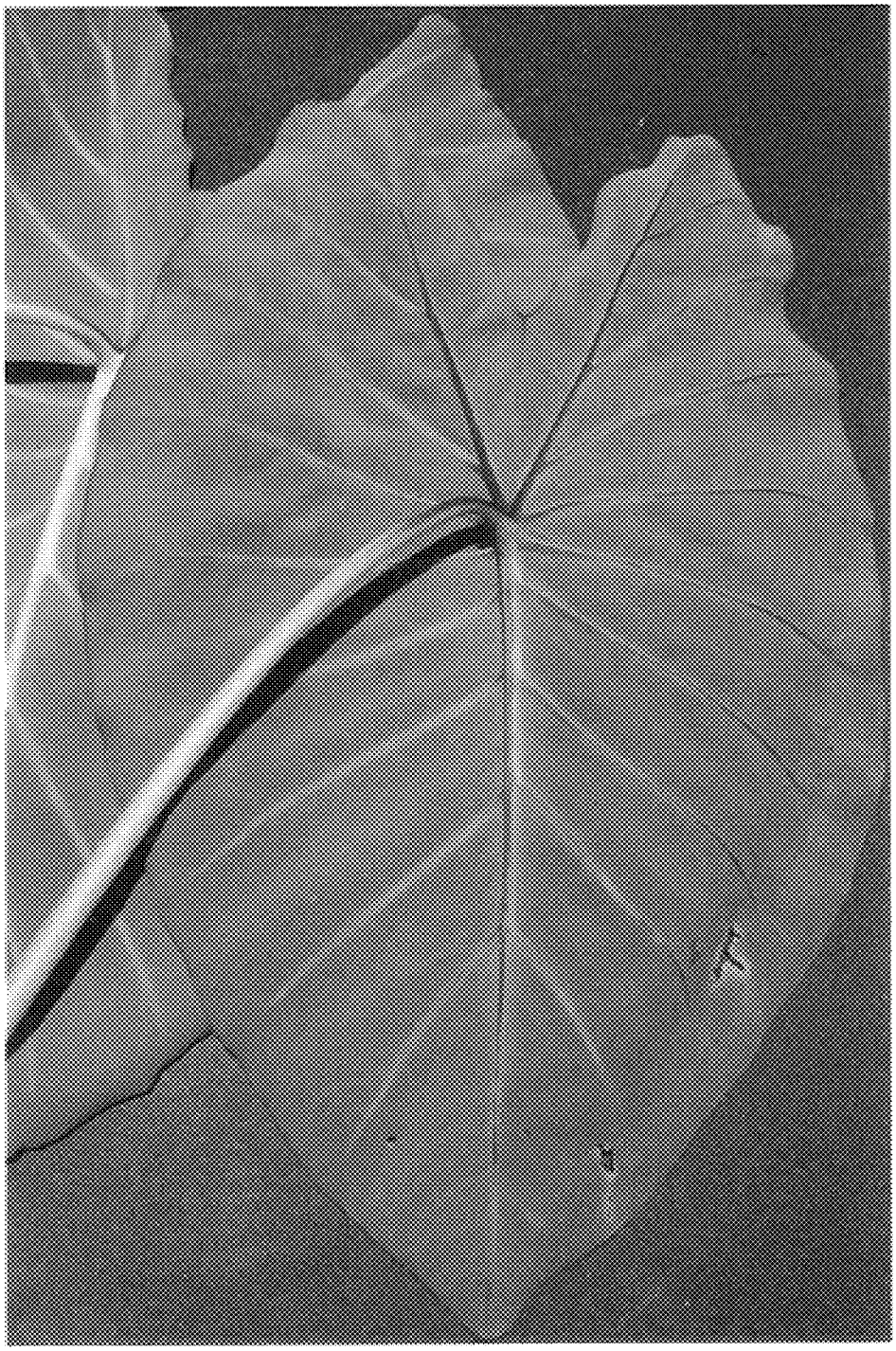
FIG 6 is a photograph of the adaxial light-green leaf surface of 'Pa'akala' with reddish-purple veins, and yellow-green petiole with reddish-purple upper portion.

*Color.*—Leaf color on the abaxial surface is dark green (R.H.S. # 137 A) and on the adaxial surface is light green (R.H.S. # 137 C) (FIG. 6). The color of the leaf margin is the same as the color of the lamina. Point of attachment of petiole to lamina (piko) on abaxial surface of leaves has a spot colored purple (R.H.S.# 61 A). The piko is large. Petioles are colored pea green (R.H.S. # 145 B) with a purple (R.H.S. #61 A) sheath margin. Petiole sap is colorless. The point of attachment of the petiole to the adaxial surface of the lamina is colored red-purple (R.H.S. # 64 A). Petioles are up to 117 cm to 130 cm long.

*Veins.*—Three principal veins radiating from the "piko", the largest a midrib extending from the "piko" to the tip of the lamina with up to 9 pairs of secondary veins radiating from it. The 2 shorter main veins extend from the "piko" to the tip of the lobes with 3 secondary veins each. Veins on the abaxial surface are light yellowish green (R.H.S. # 145 A) and on the adaxial surface of older leaves are pinkish-purple (R.H.S. # 67 B) becoming red-purple (R.H.S. #64 A) on older leaves.

Corms:

*Size.*—Main corm is large measuring 18 cm to 25 cm long with a cross-section diameter up to 15 cm to 18 cm.

*Shape.*—Ovate, free of pocket rot.

*Color.*—Outer skin tissue at base of corm is chocolate-brown (R.H.S. # 177 B), at upper portion of corm, skin is orange-brown (R.H.S. # 166 A), and upper leaves scars are reddish pink (R.H.S. # 68 C). Flesh of corm on cross-section is pinkish (R.H.S. # 62 D) with the outer 0.5 mm being intense pink (R.H.S. # 67 A). The corm fibers are of the same color as the corm flesh. Roots are pinkish white (R.H.S. # 62 D).

*Weight.*—Corm weight of mother plant is from 2.3 to 3.4 kg.

Rhizomes: The mother corm produces 3–5 suckers on closely attached rhizomes or 0.5 to 1.5 decimeter long, slender rhizomes, approximately 4–5 months after planting the huli. The daughter plant corms at harvest weight 0.2 to 0.5 kg. The outer skin tissue is chocolate-brown (R.H.S. # 177 B), the skin on the upper portion of the cormels is orange-brown (R.H.S. # 166 A), and the upper leaf scars are reddish-pink (R.H.S. # 68 C). The flesh of the corm on cross-section is pinkish (R.H.S. # 62 D) with the outer 0.5 mm being intense pink (R.H.S. # 67 A).

Inflorescence: Normally produced in late August, up to 90 cm tall, with a simple spadix subtended by a herbaceous spathe 31 cm to 43 cm long. The lower tubular portion of the spathe is partially open and drooping, is 5 cm to 7 cm long, light pea green (R.H.S. # 145 A), and the upper yellowish orange (R.H.S. # 14 C) hooked portion is 27 cm to 36 cm long. The upper 2 cm of the peduncle, which bears the flower, is red purple (R.H.S. # 59 A). The spadix is 9–14 cm long, having at the base a 3–4 cm long light green (R.H.S. # 137 C) portion producing female inflorescence, followed by 2–3 cm of pinkish white (R.H.S. # 62 C) sterile tissue, following by 3–5 cm of yellow-orange (R.H.S. # 14 D) exposed male flowers, and a yellow-orange (R.H.S. # 14 D) sterile appeandage 2 cm long. The peduncle is yellowish green (R.H.S. # 145 B) 56 cm to 85 cm long. The stigma is receptive approximately 3 days after pollen dehiscence. The pollen is yellow-orange (R.H.S. # 14 A). The fruit is a berry. Pollination does not occur naturally; fruit or seeds have not been observed.

I claim:

1. A new and distinct variety of taro plant, substantially as illustrated and described herein, that is characterized by resistance to taro leaf blight caused by *Pytophthora colocasiae*, high tolerance to root rot caused by Pythium spp., vigorous growth, extra-large mother corm size, and pinkish corm of very good flour quality and good poi and eating qualities.

* * * * *

Disclaimer

PP. 12,772 P2—Edwardo E. Trujillo, Honolulu, HI (US). TARO PLANT NAMED 'PA'AKALA'. Patent dated Jul. 16, 2002, Disclaimer filed June 16, 2006, by the Assignee, University of Hawaii.

This patent is subject to a terminal disclaimer.

*(Official Gazette, September 12, 2006)*